United States Patent
Dalko et al.

(12) 
(10) Patent No.: US 6,255,297 B1
(45) Date of Patent: Jul. 3, 2001

(54) SALICYLIC ACID DERIVATIVES AND THEIR USE IN COSMETIC OR DERMATOLOGICAL COMPOSITIONS

(75) Inventors: Maria Dalko, Gif sur Yvette; Jean-Baptiste Galey, Aulnay sous Bois, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/367,307
(22) PCT Filed: Feb. 6, 1998
(86) PCT No.: PCT/FR98/00231
  § 371 Date: Oct. 26, 1999
  § 102(e) Date: Oct. 26, 1999
(87) PCT Pub. No.: WO98/35973
  PCT Pub. Date: Aug. 20, 1998

(30) Foreign Application Priority Data

Feb. 12, 1997 (FR) .................................. 97/01617

(51) Int. Cl.$^7$ .............................. A61K 31/60; A61K 7/00
(52) U.S. Cl. ................. 514/159; 424/401; 424/78.02
(58) Field of Search .................. 424/78.02; 514/844

(56) References Cited

U.S. PATENT DOCUMENTS 5,700,784 * 12/1997 Shinojima et al. ..................... 514/24

FOREIGN PATENT DOCUMENTS 0 597 776    5/1994   (EP) .
0 649 648    4/1995   (EP) .

OTHER PUBLICATIONS

English language Derwent Abstract for EP 0 597 776.
Patent Abstracts of Japan, vol. 097, No. 002, Feb. 28, 1997 (JP 08 268872).
Patent Abstracts of Japan, vol. 097, No. 002, Feb. 28, 1997 (JP 08 268871).
Patent Abstracts of Japan, vol. 097, No. 002, Feb. 28, 1997 (JP 08 268870).
Patent Abstracts of Japan, vol. 097, No. 002, Feb. 28, 1997 (JP 08 268869).
Patent Abstracts of Japan, vol. 097, No. 002, Feb. 28, 1997 (JP 08 268868).
Patent Abstracts of Japan, vol. 097, No. 002, Feb. 28, 1997 (JP 08 268858).
Patent Abstracts of Japan, vol. 008, No. 283, Dec. 25, 1984 (JP 59 152328).

* cited by examiner

Primary Examiner—Shelley A. Dodson
Assistant Examiner—Konata M. George
(74) Attorney, Agent, or Firm—Finnegan, Henderson, Farabow, Garrett & Dunner, L.L.P.

(57) ABSTRACT

The invention relates to novel salicylic acid derivatives and to the use thereof in a cosmetic and/or dermatological composition intended for skincare, in particular to combat the signs of ageing of the skin and/or to improve the radiance of the complexion and/or to smooth out facial and/or body skin and/or to treat wrinkles and fine lines on the skin and/or to stimulate the process of epidermal renewal.

24 Claims, No Drawings

SALICYLIC ACID DERIVATIVES AND THEIR USE IN COSMETIC OR DERMATOLOGICAL COMPOSITIONS

The present invention relates to novel salicylic acid derivatives and to the use thereof in particular in the cosmetic and/or dermatological fields. They can also be used in the pharmaceutical or veterinary field. More especially, these derivatives are used in a composition intended for human skincare, in particular to combat the signs of ageing of the skin and/or to improve the radiance of the complexion and/or to smooth out facial and/or body skin and/or to treat wrinkles and fine lines on the skin and/or to stimulate the process of epidermal renewal.

People are increasingly seeking to have a more youthful, less wrinkled appearance, by using cosmetic compositions containing active agents capable of combating ageing. In the course of the process of ageing, various-signs appear on the skin, which are very characteristic of this ageing, these being reflected in particular by a change in the skin structure and functions.

The main clinical signs of ageing of the skin are, in particular, the appearance of fine lines and deep wrinkles which increase with age. Disorganization of the "grain" of the skin is observed in particular, i.e. the micro-relief is less uniform and has an anisotropic nature. Moreover, the skin complexion is generally modified and appears paler and yellower. A loss of skin firmness and tonicity is also observed.

It is thus observed that the clinical signs of ageing of the skin result essentially from dysfunctioning of the main biological mechanisms involved in the skin.

Unfortunately, the anti-ageing active agents commonly used, such as retinoids and acidic active agents, for instance hydroxy acids, have the major drawback of causing stinging, itching and tightness of the skin after they have been applied, which may lead to discomfort or intolerance. Users with sensitive skin are thus often discouraged from using these compounds.

The Applicant has thus sought active agents having the same effect as the active agents of the prior art but without posing these problems of discomfort or of intolerance.

The Applicant has discovered, surprisingly, novel salicylic acid derivatives that are suitable for skincare and make it possible in particular to combat the signs of ageing, to improve the radiance of the skin complexion, to smooth out lines on the skin and to stimulate the process of epidermal renewal, without causing any skin irritation.

Hydroxysalicylic acid derivatives are known from document EP-A-649,648. These derivatives have a different structure from the compounds of the present invention and have essentially bleaching properties.

The subject of the invention is a compound of general formula (I):

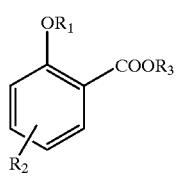

(I)

where $R_1$ represents hydrogen, a mono- or disaccharide residue, a group $R_4$—CO—, $R_4$ being chosen from linear, branched or cyclic $C_1$ to $C_{20}$ saturated alkyl groups or $C_3$ to $C_{20}$ unsaturated alkyl groups, the said alkyl groups optionally being substituted;

$R_2$ represents hydrogen or a group $R_5$—CO—, $R_5$ being chosen from linear or branched, saturated or unsaturated, optionally substituted $C_1$ to $C_{20}$ alkyl groups;

$R_3$ represents hydrogen, a linear or branched, saturated or unsaturated, optionally substituted $C_1$ to $C_{20}$ alkyl group, or a mono- or disaccharide residue, on condition that at least one of the radicals $R_1$ or $R_3$ represents a mono- or disaccharide residue and that, when $R_2$ is hydrogen, $R_1$ is other than —COCH$_3$.

Advantageously, $R_1$ is hydrogen and $R_3$ represents a mono- or disaccharide residue, and in particular a galactose residue.

$R_2$ can be in an ortho or para position relative to the group $OR_1$. Preferably, $R_2$ is in the para position relative to the group $OR_1$ and represents hydrogen or a group $R_5$—CO— where $R_5$ is a saturated alkyl group containing from 3 to 11 carbon atoms. $R_5$ can be chosen in particular from linear or branched octyl, decyl, hexyl and dodecyl groups.

As substituents on the alkyl groups $R_3$, $R_4$ and $R_5$, mention may be made of halogen atoms, the trifluoromethyl group, the hydroxyl group in free form or esterified with an acid having from 1 to 6 carbon atoms, or alternatively carboxyl groups, free or esterified with a lower alcohol having from 1 to 6 carbon atoms.

Preferably, the compound according to the invention is, in particular, 3,4,5,6-tetrahydroxytetrahydropyran-2-ylmethyl 2-hydroxybenzoate, 3,4,5,6-tetrahydroxytetrahydropyran-2-ylmethyl 2-hydroxy-5-octanoylbenzoate or 2-(1,2-dihydroethyl)-4,5-dihydroxytetrahydrofuran-3-yl 2-hydroxy-5-octanoylbenzoate.

The compounds of formula (I) are novel except for 2-O-β-D-glucopyranosylsalicylic acid and glucose salicylate, which are known as analgesics for treating stomach aches and ulcers in patent JP 59,152,328. They are obtained according to a standard synthetic process which consists in reacting the protected (for example in the form of acetonide or by benzylation) sugar and the acid chloride of the salicylic derivative, or in reacting the salicylic derivative, protected in ester form, and the acid chloride of the protected sugar, and then in deprotecting the compound obtained, for example in acidic medium in the case where the sugar was protected by an acetonide function, or by hydrogenolysis in the case where the sugar was perbenzylated.

The subject of the invention is also a composition comprising at least one compound as defined above. This composition is, in particular, a topical composition, in particular a cosmetic and/or dermatological composition. In this case, it contains a physiologically acceptable medium. The expression physiologically acceptable medium is understood to refer to a medium which is compatible with the skin, mucous membranes, the nails and/or the hair.

The compounds according to the invention can be present in a composition according to the invention in an amount ranging from 0.001 to 30%, preferably from 0.01 to 10% and better still from 0.1 to 5%, relative to the total weight of the composition.

The compositions containing a compound of formula (I) can be in any pharmaceutical form usually suitable for topical application, and, for example, in the form of an aqueous, alcoholic, aqueous-alcoholic or oily solution, an aqueous or oily gel, an anhydrous solid composition, a dispersion of the lotion or serum type, an emulsion of the water-in-oil (W/O), oil-in-water (O/W) or multiple (W/O/W or O/W/O) type, a microemulsion or a dispersion of vesicles of ionic and/or nonionic type. These compositions are prepared according to the usual methods.

These compositions can comprise at least one additive chosen from fatty substances, preserving agents, gelling agents, fragrances, silicones, surfactants, water, antioxidants, fillers, screening agents, physiologically acceptable active agents such as moisturizers, vitamins, anti-ageing active agents other than the compounds of formula (I), and mixtures thereof.

The fatty substances can be chosen from oils such as jojoba oil, liquid petroleum jelly, isopropyl palmitate, silicones (cyclopentadimethylsiloxane), waxes such as sipol wax, carnauba wax, fatty acids, fatty alcohols (stearyl alcohol) and mixtures thereof.

The amounts of the various constituents of the compositions according to the invention are those used conventionally in the fields considered.

These compositions especially constitute care creams or treatment creams for the face, for the hands or for the body (for example day creams or night creams), make-up products such as foundations, bodymilks for protection or care, and skincare lotions, gels or mousses.

The subject of the invention is also a use of the compound of formula (I) in and/or for the manufacture of a cosmetic and/or dermatological composition intended for skincare.

The subject of the invention is also a use of the compound of formula (I) in and/or for the manufacture of a cosmetic and/or dermatological composition intended to combat the signs of ageing of the skin and/or to improve the radiance of the complexion and/or to smooth out facial skin and/or body skin and/or to treat wrinkles and fine lines on the skin and/or to stimulate the process of epidermal renewal.

Lastly, the subject of the invention is a process for the cosmetic treatment of the signs of ageing of the skin, which consists in applying the compound of formula (I) in a physiologically acceptable medium to skin showing these signs.

Other characteristics and advantages of the invention will emerge more clearly from the examples which follow, which are given by way of non-limiting illustration.

The following Examples 1 to 3 illustrate the process for the preparation of the derivatives in accordance with the invention.

EXAMPLE 1

Preparation of 3,4,5,6-tetrahydroxytetrahydropyran-2-ylmethyl 2-hydroxybenzoate

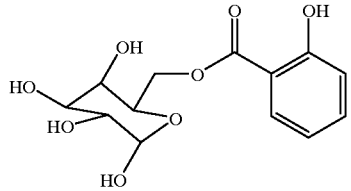

Synthetic Scheme (see Annex 1)

Step 1: Reaction of the Acid Chloride with the Protected Galactose

A solution of 6 ml of dichloromethane containing 640 mg of acetyl salicylic acid chloride is added, at 0° C. under argon, to a solution of 10 ml of dichloromethane containing 700 mg of diisopropyl-D-galactose and 1.5 ml of triethylamine. The solution is stirred for 5 h at room temperature. A further 240 mg of acid chloride and 0.4 ml of triethylamine in 5 ml of dichloromethane are added and the mixture is stirred for 1 h. 20 ml of saturated $NaHCO_3$ are then added, after which the organic phase is separated out and is dried over sodium sulphate. The product is purified by chromatography on a column of silica.

0.9 g of a colourless oil is obtained whose $^1H$, $^{13}C$ and IR NMR spectra are in agreement with the expected structure.

Step 2: Deprotection 105 mg of the product obtained in the above step are dissolved in 10 ml of a 1/1 trifluoroacetic acid/water mixture. The solution is stirred for 2 h 45 at 70° C. and then evaporated to dryness. The residue is purified by chromatography on a column of silica.

A colourless oil is obtained whose $^1H$ and $^{13}C$ NMR spectra are in agreement with the expected structure.

The yield for the synthesis is 52%.

Elemental analysis:

|  | C | H | O |
|---|---|---|---|
| Theory | 52.0 | 5.37 | 42.63 |
| Found | 51.64 | 5.32 | 42.39 |

EXAMPLE 2

Preparation of 3,4,5,6-tetrahydroxytetrahydropyran-2-ylmethyl 2-hydroxy-5-octanoylbenzoate According to a synthetic scheme similar to that of Example 1, 3,4,5,6-tetrahydroxytetrahydropyran-2-ylmethyl 2-hydroxy-5-octanoylbenzoate of the formula below was synthesized:

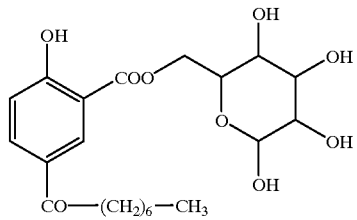

Step 1: Preparation of the Acid Chloride

To a solution of 5 g of 2-acetoxy-5-octanoylbenzoic acid in 60 ml of anhydrous toluene under argon are added 16.3 ml of a 2M solution of oxalyl chloride in toluene. One drop of DMF is then added, after which the medium is stirred for 30 minutes at room temperature. The solution is evaporated and a yellow oil is obtained, which is used directly in the next step.

Step 2: Reaction of the Acid Chloride with the Protected Galactose

A solution of 50 ml of dichloromethane containing 7.9 g of diisopropyl-D-galactose and 22.6 ml of triethylamine is added, at 0° C. under argon, to a solution of 7.9 g of the acid chloride obtained in the first step in 50 ml of dichloromethane. The solution is stirred for 60 h at room temperature. 100 ml of saturated $NaHCO_3$ are then added, after which the organic phase is separated out and dried over sodium sulphate. The product is purified by chromatography on a column of silica.

13.5 g of a mixture containing the expected product contaminated with the corresponding deacetylation product are obtained.

Step 3: Deprotection 1.06 g of the product obtained in the above step are dissolved in 25 ml of a 3/7 trifluoroacetic acid/water mixture. The solution is stirred for 4 h 30 at 60° C. and then evaporated to dryness. The residue is taken up in 50 ml of ethyl acetate and washed with water. After purification by chromatography on a column of silica, a white solid is obtained whose $^1$H and $^{13}$C NMR spectra are in agreement with the structure of 3,4,5,6-tetrahydroxytetrahydropyran-2-ylmethyl 2-hydroxy-5-octanoylbenzoate.

Elemental analysis:

|        | C     | H    | O     |
|--------|-------|------|-------|
| Theory | 59.14 | 7.09 | 33.76 |
| Found  | 58.38 | 7.06 | 34.12 |

EXAMPLE 3

Preparation of 2-(1,2-dihydroethyl)-4,5-dihydroxytetrahydrofuran-3-yl 2-hydroxy-5-octanoylbenzoate According to a synthetic scheme similar to that of Example 1, 2-(1,2-dihydroethyl)-4,5-dihydroxytetrahydrofuran-3-yl 2-hydroxy-5-octanoylbenzoate was synthesized using 1,2,3,4-di-O-isopropylidene-D-galactopyranose. The $^1$H and $^{13}$C NMR spectra of the product obtained are in agreement with the expected structure.

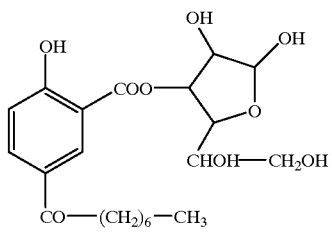

Elemental analysis:

|        | C     | H    | O     |
|--------|-------|------|-------|
| Theory | 59.14 | 7.09 | 33.76 |
| Found  | 58.81 | 7.16 | 33.45 |

TEST: The Applicant has observed that stimulation of the process of epidermal renewal, consisting in removing the surface cells from the skin, led to a smoothing-out of the lines, revival of the complexion and a reduction in wrinkles and fine lines. Thus, the Applicant has determined the efficacy of the treatment of the signs of ageing for the compounds according to the invention by carrying out an in vitro test of cell detachment.

This in vitro test was carried out on keratinocytes using the compounds of Examples 2 and 3. The principle of the test lies in the fact that cell detachment induces the release of corneocytes. The ageing-treatment power of the product tested will be proportionately greater the larger the number of corneocytes released.

The test procedure was as follows: keratinocytes were obtained from skin biopsies by separation of the epidermis, and they were then dissociated by enzymatic action with trypsin and cultured at the concentration of $2 \times 10^{-5}$ cells/ml. Growth and differentiation of the keratinocytes were obtained by culturing for 10 to 20 days in specific medium.

Next, after removal of the culture medium, the product to be tested was added and the activity of the product evaluated. To do this, two samples were taken at T0 and T60, i.e. before addition of the product and 60 minutes after this addition, and the samples thus taken were analysed with a flow cytometer in order to count the corneocyte population. With a flow cytometer, the populations of corneocytes and of keratinocytes are differentiated by treatment with acridine orange which is specific for cellular DNA, which binds to the cell nucleus and thus exclusively reveals the presence of the keratinocytes.

The cell detachment index is determined by the difference between T60 and T0.

The same measurement was taken for a control containing no product to be tested since the experiment inevitably produces the release of corneocytes, even in the absence of active agent. The variation of the control arbitrarily set the standard at 100%.

The results are collated in the table below:

| Control | Compound of Example 2<br>$5 \times 10^{-5}$ M | Compound of Example 3<br>$5 \times 10^{-5}$ M |
|---------|-----------------------------------------------|-----------------------------------------------|
| 100%    | 214.7%                                        | 207.1%                                        |

These results show that the compounds according to the invention promote cell detachment and thus make it possible to smooth out the skin and to attenuate, or even eliminate, the signs of ageing.

The following examples illustrate the cosmetic or dermatological compositions according to the invention. The amounts are given as a percentage by weight.

FORMULATION EXAMPLE 1
Facial Care Cream

| compound of Example 2 | 1% |
|---|---|
| sodium stearate (emulsifier) | 3% |
| liquid petroleum jelly | 6% |
| preserving agent | 0.05% |
| cyclopentadimethylsiloxane | 5% |
| stearyl alcohol | 1% |
| fragrance | 1% |
| water | qs 100% |

Daily use of this cream on the face allows a smoother, younger skin to be obtained.

FORMULATION EXAMPLE 2
Body care cream

| compound of Example 1 | 1% |
|---|---|
| jojoba oil | 13% |
| isopropyl palmitate | 2% |
| polyethylene glycol stearate (emulsifier) | 3% |
| glycerol (moisturizer) | 15% |
| preserving agent | 0.5% |
| fragrance | 1% |
| water | qs 100% |

A care cream is obtained which acts against ageing without irritating the skin.

ANNEX 1

Synthetic Scheme of Example 1

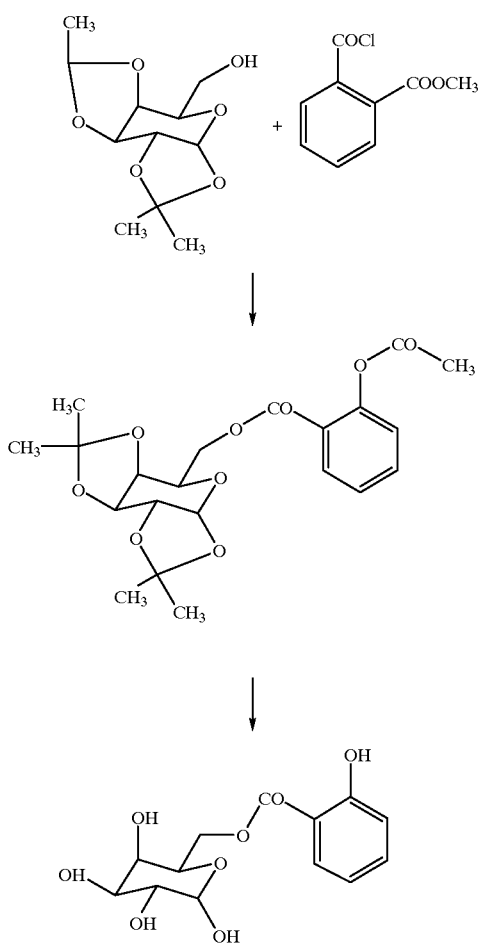

What is claimed is:

1. A compound of general formula (I):

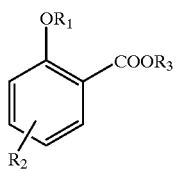

in which:
- $R_1$ is chosen from hydrogen, monosaccharide residues, disaccharide residues, and radicals of formula $R_4$—CO—, wherein $R_4$ is chosen from linear, branched, and cyclic $C_1$ to $C_{20}$ alkyl groups, said alkyl groups are saturated or unsaturated, and substituted or unsubstituted;
- $R_2$ is chosen from hydrogen and carbonyl radicals of formula $R_5$—CO—, wherein $R_5$ is chosen from linear and branched $C_1$ to $C_{20}$ alkyl groups, said alkyl groups are saturated or unsaturated, and substituted or unsubstituted;
- $R_3$ is chosen from hydrogen, linear $C_1$ to $C_{20}$ alkyl groups, branched $C_1$ to $C_{20}$ alkyl groups, monosaccharide residues, and disaccharide residues, said alkyl groups are saturated or unsaturated, and substituted or unsubstituted;

provided that: 1) at least one of the radicals $R_1$ or $R_3$ is chosen from mono- and disaccharide residues, 2) when $R_2$ is hydrogen, $R_1$ is other than —COCH$_3$, and 3) the compound of general formula (1) is not 2-O-β-D-glucopyranosyl salicylic acid and glucose salicylate.

2. A compound according to claim 1, wherein $R_1$ is hydrogen.

3. A compound according to claim 1, wherein $R_2$ is chosen from hydrogen and radicals of formula $R_5$—CO—, wherein $R_5$ is chosen from $C_3$–$C_{11}$ saturated alkyl groups.

4. A compound according to claim 1, wherein $R_2$ is chosen from linear or branched octyl, decyl, hexyl and dodecyl groups.

5. A compound according to claim 1, wherein $R_3$ is chosen from mono- and disaccharide residues.

6. A compound according to claim 1, wherein said compound is chosen from 3,4,5,6-tetrahydroxytetrahydropyran-2-ylmethyl 2-hydroxybenzoate, 3,4,5,6-tetrahydroxytetrahydropyran-2-ylmethyl 2-hydroxy-5-octanoylbenzoate and 2-(1,2-dihydroethyl)-4,5-dihydroxytetrahydrofuran-3-yl 2-hydroxy-5-octanoylbenzoate.

7. A composition comprising a physiologically acceptable medium and at least one compound of general formula (I):

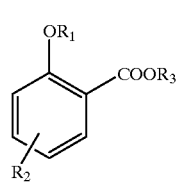

in which:
- $R_1$ is chosen from hydrogen, monosaccharide residues, disaccharide residues, and radicals of formula $R_4$—CO—, wherein $R_4$ is chosen from linear, branched, and cyclic $C_1$ to $C_{20}$ alkyl groups, said alkyl groups are saturated or unsaturated, and substituted or unsubstituted;
- $R_2$ is chosen from hydrogen and carbonyl radicals of formula $R_5$—CO—, wherein $R_5$ is chosen from linear and branched $C_1$ to $C_{20}$ alkyl groups, said alkyl groups are saturated or unsaturated, and substituted or unsubstituted;
- $R_3$ is chosen from hydrogen, linear $C_1$ to $C_{20}$ alkyl groups, branched $C_1$ to $C_{20}$ alkyl groups, monosaccharide residues, and disaccharide residues, said alkyl groups are saturated or unsaturated, and substituted or unsubstituted;

provided that: 1) at least one of the radicals $R_1$ or $R_3$ is chosen from mono- and disaccharide residues, and 2) when $R_2$ is hydrogen, $R_1$ is other than —COCH$_3$.

8. A composition according to claim 7, wherein said at least one compound of general formula (1) is present in an amount ranging from 0.001 to 30% by weight relative to the total weight of the composition.

9. A composition according to claim 8, wherein said at least one compound is present in said composition in an amount ranging from 0.01 to 10% by weight.

10. A composition according to claim 9, wherein said at least one compound is present in said composition in an amount ranging from 0.1 to 5% by weight.

11. A cosmetic composition comprising a physiologically acceptable medium and at least one compound of general formula (I):

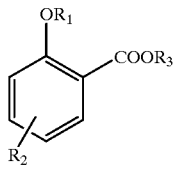

in which:

$R_1$ is chosen from hydrogen, monosaccharide residues, disaccharide residues, and radicals of formula $R_4$—CO—, wherein $R_4$ is chosen from linear, branched, and cyclic $C_1$ to $C_{20}$ alkyl groups, said alkyl groups are saturated or unsaturated, and substituted or unsubstituted;

$R_2$ is chosen from hydrogen and carbonyl radicals of formula $R_5$—CO—, wherein $R_5$ is chosen from linear and branched $C_1$ to $C_{20}$ alkyl groups, said alkyl groups are saturated or unsaturated, and substituted or unsubstituted;

$R_3$ is chosen from hydrogen, linear $C_1$ to $C_{20}$ alkyl groups, branched $C_1$ to $C_{20}$ alkyl groups, monosaccharide residues, and disaccharide residues, said alkyl groups are saturated or unsaturated, and substituted or unsubstituted;

provided that: 1) at least one of the radicals $R_1$ or $R_3$ is chosen from mono- and disaccharide residues, said residues terminate at a carbon, and 2) when $R_2$ is hydrogen, $R_1$ is other than —COCH$_3$.

12. A composition according to claim 11, wherein said composition further comprises at least one additive chosen from fatty substances, preserving agents, gelling agents, fragrances, silicones, surfactants, water, antioxidants, fillers, emulsifiers, screening agents, conditioning agents, moisturizing agents, and physiologically acceptable active agents.

13. A composition according to claim 11, wherein said composition is in the form of a solution, a gel, a dispersion, an emulsion, a microemulsion or a dispersion of iconic vesicles, nonionic vesicles, or mixtures thereof.

14. A composition according to claim 11, wherein said at least one compound is present in said composition in an amount ranging from 0.001 to 30% by weight relative to the total weight of said composition.

15. A composition according to claim 14, wherein said at least one compound is present in said composition in an amount ranging from 0.01 to 10% by weight.

16. A composition according to claim 15, wherein said at least one compound is present in said composition in an amount ranging from 0.1 to 5% by weight.

17. A process for the manufacture of a cosmetic skin care composition comprising, providing a physiologically acceptable medium, and including with said physiological acceptable medium at least one compound of general formula (I):

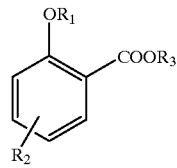

in which $R_1$ is chosen from hydrogen, monosaccharide residues, disaccharide residues, and radicals of formula $R_4$—CO—, wherein $R_4$ is chosen from linear, branched, and cyclic $C_1$ to $C_{20}$ alkyl groups, said alkyl groups are saturated or unsaturated, and substituted or unsubstituted;

$R_2$ is chosen from hydrogen and radicals of formula $R_5$—CO—, wherein $R_5$ is chosen from linear and branched $C_1$ to $C_{20}$ alkyl groups, said alkyl groups are saturated or unsaturated, and substituted or unsubstituted;

$R_3$ is chosen from hydrogen, linear $C_1$ to $C_{20}$ alkyl groups, branched $C_1$ to $C_{20}$ alkyl groups, monosaccharide residues, and disaccharide residues, said alkyl groups are saturated or unsaturated, and substituted or unsubstituted;

provided that: 1) at least one of the radicals $R_1$ or $R_3$ is chosen from mono- and disaccharide residues, and 2) when $R_2$ is hydrogen, $R_1$ is other than —COCH$_3$.

18. A process for cosmetic treatment of the signs of aging of the skin, comprising applying to skin showing these signs at least one compound of general formula (I) in a physiologically acceptable medium:

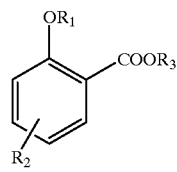

in which:

$R_1$ is chosen from hydrogen, monosaccharide residues, disaccharide residues, and radicals of formula $R_4$—CO—, wherein $R_4$ is chosen from linear, branched, and cyclic $C_1$ to $C_{20}$ alkyl groups, said alkyl groups are saturated or unsaturated, and substituted or unsubstituted;

$R_2$ is chosen from hydrogen and radicals of formula $R_5$—CO—, wherein $R_5$ is chosen from linear and branched $C_1$ to $C_{20}$ alkyl groups, said alkyl groups are saturated or unsaturated, and substituted or unsubstituted;

$R_3$ is chosen from hydrogen, linear $C_1$ to $C_{20}$ alkyl groups, branched $C_1$ to $C_{20}$ alkyl groups, monosaccharide residues, and disaccharide residues, said alkyl groups are saturated or unsaturated, and substituted or unsubstituted;

provided that: 1) at least one of the radicals $R_1$ or $R_3$ is chosen from mono- and disaccharide residues, and 2) when $R_2$ is hydrogen, $R_1$ is other than —COCH$_3$.

19. A dermatological composition comprising a physiologically acceptable medium and at least one compound of general formula (I):

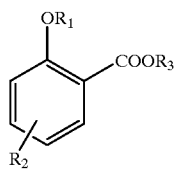

(I)

in which:
R$_1$ is chosen from hydrogen, monosaccharide residues, disaccharide residues, and radicals of formula R$_4$—CO—, wherein R$_4$ is chosen from linear, branched, and cyclic C$_1$ to C$_{20}$ alkyl groups, said alkyl groups are saturated or unsaturated, and substituted or unsubstituted;

R$_2$ is chosen from hydrogen and carbonyl radicals of formula R$_5$—CO—, wherein R$_5$ is chosen from linear and branched C$_1$ to C$_{20}$ alkyl groups, said alkyl groups are saturated or unsaturated, and substituted or unsubstituted;

R$_3$ is chosen from hydrogen, linear C$_1$ to C$_{20}$ alkyl groups, branched C$_1$ to C$_{20}$ alkyl groups, mnonosaccharide residues, and disaccharide residues, said alkyl groups are saturated or unsaturated, and substituted or unsubstituted;

provided that: 1) at least one of the radicals R$_1$ or R$_3$ is chosen from mono- and disaccharide residues, said residues terminate at a carbon, and 2) when R$_2$ is hydrogen, R$_1$ is other than —COCH$_3$.

20. A composition according to claim 19, wherein said at least one compound is present in said composition in an amount ranging from 0.001 to 30% by weight relative to the total weight of said composition.

21. A composition according to claim 20, wherein said at least one compound is present in said composition in an amount ranging from 0.01 to 10% by weight.

22. A composition according to claim 21, wherein said at least one compound is present in said composition in an amount ranging from 0.1 to 5% by weight.

23. A process for the manufacture of a dermatological skin care composition comprising, providing a physiologically acceptable medium, and including with said physiological acceptable medium at least one compound of general formula (I):

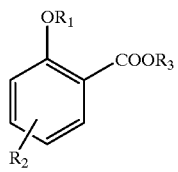

(I)

in which:
R$_1$ is chosen from hydrogen, monosaccharide residues, disaccharide residues, and radicals of formula R$_4$—CO—, wherein R$_4$ is chosen from linear, branched, and cyclic C$_1$ to C$_{20}$ alkyl groups, said alkyl groups are saturated or unsaturated, and substituted or unsubstituted;

R$_2$ is chosen from hydrogen and radicals of formula R$_5$—CO—, wherein R$_5$ is chosen from linear and branched C$_1$ to C$_{20}$ alkyl groups, said alkyl groups are saturated or unsaturated, and substituted or unsubstituted;

R$_3$ is chosen from hydrogen, linear C$_1$ to C$_{20}$ alkyl groups, branched C$_1$ to C$_{20}$ alkyl groups, monosaccharide residues, and disaccharide residues, said alkyl groups are saturated or unsaturated, and substituted or unsubstituted;

provided that: 1) at least one of the radicals R$_1$ or R$_3$ is chosen from mono- and disaccharide residues, and 2) when R$_2$ is hydrogen, R$_1$ is other than —COCH$_3$.

24. A process for combating the signs of aging of the skin, improving the radiance of the complexion, smoothing out facial or body skin, treating wrinkles and fine lines on the skin, or stimulating the process of epidermal renewal, comprising applying to the skin a cosmetic or dermatological composition comprising a physiologically acceptable medium and at least one compound of general formula (I):

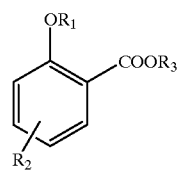

(I)

in which:
R$_1$ is chosen from hydrogen, monosaccharide residues, disaccharide residues, and radicals of formula R$_4$—CO—, wherein R$_4$ is chosen from linear, branched, and cyclic C$_1$ to C$_{20}$ alkyl groups, said alkyl groups are saturated or unsaturated, and substituted or unsubstituted;

R$_2$ is chosen from hydrogen and radicals of formula R$_5$—CO—, wherein R$_5$ is chosen from linear and branched C$_1$ to C$_{20}$ alkyl groups, said alkyl groups are saturated or unsaturated, and substituted or unsubstituted;

R$_3$ is chosen from hydrogen, linear C$_1$ to C$_{20}$ alkyl groups, branched C$_1$ to C$_{20}$ alkyl groups, monosaccharide residues, and disaccharide residues, said alkyl groups are saturated or unsaturated, and substituted or unsubstituted;

provided that: 1) at least one of the radicals R$_1$ or R$_3$ is chosen from mono- and disaccharide residues, and 2) when R$_2$ is hydrogen, R$_1$ is other than —COCH3.

* * * * *

UNITED STATES PATENT AND TRADEMARK OFFICE
CERTIFICATE OF CORRECTION

PATENT NO. : 6,255,297 B1
DATED : July 3, 2001
INVENTOR(S) : Dalko et al.

It is certified that error appears in the above-identified patent and that said Letters Patent is hereby corrected as shown below:

Column 12,
Line 56, please delete "—COCH3" and replace with -- —COCH$_3$ --

Signed and Sealed this

Sixteenth Day of July, 2002

Attest:

JAMES E. ROGAN
Attesting Officer         Director of the United States Patent and Trademark Office